United States Patent
Cohade et al.

(10) Patent No.: US 11,896,463 B2
(45) Date of Patent: Feb. 13, 2024

(54) OPTIMIZED COMPRESSION BANDAGE AND KIT USING SAID BANDAGE

(71) Applicant: URGO RECHERCHE INNOVATION ET DEVELOPPEMENT, Chenove (FR)

(72) Inventors: Céline Cohade, Saint-Jean-Bonnefonds (FR); David Grange, Bellagarde en Forez (FR); Serge Lecomte, Dijon (FR); Magali Roblot, Chenove (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 183 days.

(21) Appl. No.: 15/778,406

(22) PCT Filed: Nov. 25, 2016

(86) PCT No.: PCT/FR2016/053105
§ 371 (c)(1),
(2) Date: May 23, 2018

(87) PCT Pub. No.: WO2017/089731
PCT Pub. Date: Jun. 1, 2017

(65) Prior Publication Data
US 2018/0344531 A1 Dec. 6, 2018

(30) Foreign Application Priority Data
Nov. 26, 2015 (FR) ..................... 1561402

(51) Int. Cl.
*A61F 13/00* (2006.01)
*D04B 21/18* (2006.01)

(52) U.S. Cl.
CPC .. *A61F 13/00038* (2013.01); *A61F 13/00017* (2013.01); *D04B 21/18* (2013.01);
(Continued)

(58) Field of Classification Search
CPC .......... A61F 13/00038; A61F 13/00017; A61F 13/00008; A61F 2013/0028; A61F 13/025;
(Continued)

(56) References Cited

U.S. PATENT DOCUMENTS 5,385,036 A 1/1995 Spillane et al.
6,156,424 A * 12/2000 Taylor ................... A61L 15/585
427/207.1

(Continued)

FOREIGN PATENT DOCUMENTS

GB 2473321 3/2011
WO 9516416 6/1995
(Continued)

OTHER PUBLICATIONS

Nylon 101, Laird Plastics, https://www.lairdplastics.com/product/materials/nylon/3350-nylon-101 (Year: 2020).*
(Continued)

*Primary Examiner* — Ophelia A Hawthorne
(74) *Attorney, Agent, or Firm* — Hamre, Schumann, Mueller & Larson, P.C.

(57) ABSTRACT

A compression bandage in the form of a knit obtained by warp stitch technology on the basis of synthetic yarns and comprising two textile surfaces of respective textile structures that may be identical or different, the surfaces being interconnected by spacer yarns, each surface including elastic yarns, the bandage being characterized in that said knit presents:
longitudinal stretch measured in compliance with the standard EN 14704-1 lying in the range 30% to 160%; and
threshold shear stress greater than or equal to 2800 Pa.

11 Claims, 3 Drawing Sheets

Figure 1:
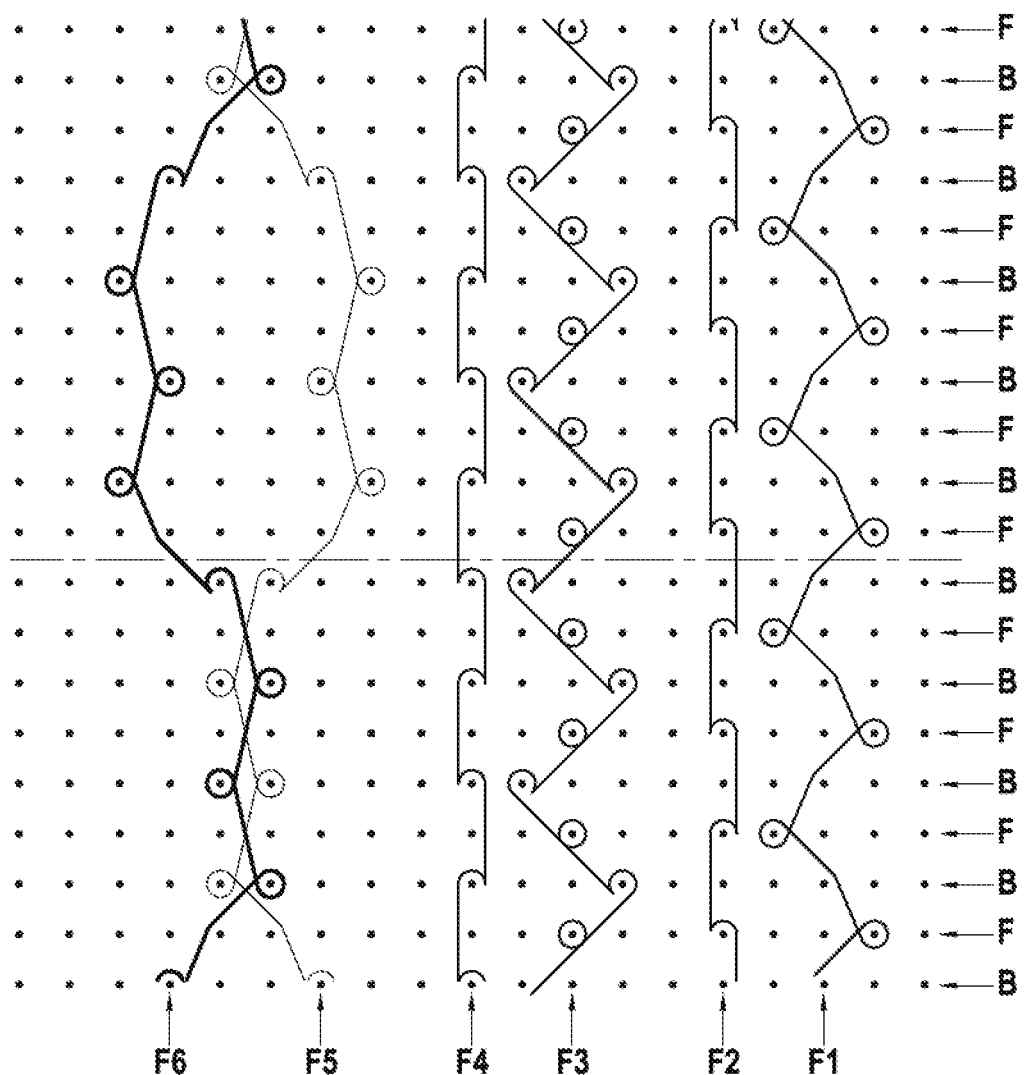

(52) U.S. Cl.
CPC ...... *D10B 2331/02* (2013.01); *D10B 2331/04* (2013.01); *D10B 2403/0213* (2013.01); *D10B 2509/028* (2013.01)

(58) Field of Classification Search
CPC ........ A61F 13/0273; A61F 2013/15292; A61F 2013/15284; A61F 2013/15357; A61F 13/062; A61F 13/085; A61F 5/0109; A61F 13/108; B32B 2307/51; B32B 5/245; B32B 5/26; D10B 2509/022; D10B 2509/028; A43B 1/04; D04B 1/104; D04B 1/16; D04B 1/18; D04B 21/10; D04B 21/16; D04B 21/18; A61L 15/46; A61L 15/16
See application file for complete search history.

(56) References Cited

U.S. PATENT DOCUMENTS

| | | | |
|---|---|---|---|
| 2002/0099318 A1* | 7/2002 | Suehr | A61F 13/08 602/76 |
| 2010/0305535 A1* | 12/2010 | Leeming | A61F 13/069 602/44 |
| 2011/0071453 A1* | 3/2011 | Schuren | A61F 13/069 602/77 |
| 2014/0080373 A1* | 3/2014 | Keitch | D04B 21/12 66/190 |
| 2016/0030251 A1* | 2/2016 | Schuren | A61F 5/0109 602/75 |
| 2016/0242964 A1* | 8/2016 | Rapp | A61F 13/025 |
| 2017/0273830 A1* | 9/2017 | Hitschmann | A61F 13/108 |

FOREIGN PATENT DOCUMENTS

| | | | |
|---|---|---|---|
| WO | WO-9516416 A1 * | 6/1995 | ....... A61F 13/00008 |
| WO | 200971894 | 6/2009 | |

OTHER PUBLICATIONS

International Search Report issued in International Application in PCT/FR2016/053105 dated Apr. 4, 2017 (5 pages).
Written Opinion issued in International Application in PCT/FR2016/053105 dated Apr. 4, 2017 (7 pages).

* cited by examiner

OPTIMIZED COMPRESSION BANDAGE AND KIT USING SAID BANDAGE

GENERAL TECHNICAL FIELD

The present invention relates to an optimized compression bandage, presenting longitudinal stretch in the range 30% to 160%, that is a three-dimensional (3D) knit obtained using "warp stitch" technology, that does not include latex or adhesive, and that does not slacken, thereby making it possible to conserve its therapeutic effectiveness and to avoid it slipping over time.

STATE OF THE ART

The use of various compression systems is known for treating pathologies involving veins, such as for example venous insufficiency, treating varicose veins and leg ulcers, or indeed preventing vein thrombosis or treating lymphedema. Those systems are constituted by one or more bandages that apply pressure on the limb for treatment.

In order to be effective, the system must make it possible to apply simultaneously:
- both relatively low pressure referred to as "rest" pressure when the muscle is relaxed so as to be comfortable and in particular bearable overnight; and
- also relatively high pressure referred to as "working" pressure when the muscle is tensioned or during movement, in particular while walking.

This pressure difference between working pressure and rest pressure needs to be sufficient to enhance venous reflux. It is generally considered that a pressure difference at 24 hours lying in the range 15 millimeters of mercury (mmHg) to mmHg is necessary for reestablishing correct venous flow.

Nevertheless, depending on the pathology, whether it involves treatment for legs without severe ulcers, difficult treatment on leg damaged by edema, or treatment of a mixed venous and arterial ulcer, this range of values may extend to mmHg to mmHg or even mmHg to 40 mmHg.

Specialists classify the compression bandages that are in use in two large categories depending on their stretch; there are bandages that are said to be of "short-stretch" and there are bandages that are said to be of "long stretch".

This classification is based on measuring the longitudinal stretch of the bandage as defined in method A § 9.1 of the standard EN 14704-1 when the bandage is subjected to a maximum traction force of 6 newtons per centimeter (N/cm).

The measurement is performed under the following conditions.

A testpiece of the material for testing having a width of 50 millimeters (mm) and a length lying in the range 250 mm to 300 mm is cut out and positioned without prestress in the jaws of an electronic constant rate of extension (CRE) force test instrument (e.g. of the MTS trademark) so as to have a width of 50 mm and a reference useful length of 200 mm. The instrument stretches the testpiece at a rate of 100 millimeters per minute (mm/min) up to a maximum force of 6 N/cm, and then the moving jaw returns to its initial position, returning at the same speed of 100 mm/min. This cycle is performed five times and the stretch obtained on the fifth cycle, expressed as a percentage, is calculated directly by the apparatus. The operation is repeated on five testpieces, and then the average value is calculated, which defines the longitudinal stretch of the bandage.

The transverse stretch of the bandage can be evaluated using the same protocol.

Short Stretch Bandages

On the basis of that test in accordance with the standard EN 14704-1 used as a reference, it is considered that a compression bandage is a bandage having "short stretch" when its longitudinal stretch is less than or equal to 100%.

Such bandages exert low rest pressure and a high working pressure. They thus present a large pressure difference, in particular during movements, e.g. while walking.

Long Stretch Bandages

On the basis of that test in accordance with the standard EN 14704-1 used as a reference, it is considered that a compression bandage is a bandage having "long stretch" when its longitudinal stretch is greater than 100%.

These bandages are easier to put on since they present greater extensibility.

Long stretch bandages lead to small variations in pressure between rest and working, and to little variation in pressure during movements, e.g. while walking. They are found to be less effective than short stretch bandages. In contrast, because of the small pressure difference, they are subjected during movements to stresses of smaller force than are short stretch bandages, and they therefore present a risk of slackening and slipping along the leg that is smaller than the risk for short stretch bandages.

It is nowadays recognized that the compression systems providing the best performance in terms of ease and speed of putting on and in terms of therapeutic effectiveness are those that comprise at most two bandages and at least one "short stretch" compression bandage.

By way of example, mention may be made of products sold under the names ACTICO, K2, and Coban 2, respectively by the suppliers Activa, Laboratoires URGO, and 3M.

The ACTICO system is constituted by a self-adhesive short stretch bandage that is wound on a strip of cotton wool previously wound on the leg. The cotton wool serves to distribute pressure over the surface of the limb, and/or to protect bony projections by virtue of its thickness, and to absorb any exudate if the bandage is placed on an open wound, e.g. if there are leg ulcers.

The system K2® sold by the supplier Laboratoires URGO is constituted by a first bandage (sold under the name Ktech®), which is a short stretch bandage constituted by a layer of cotton wool that comes into contact with the skin and that is needled to an elastic knit, and a second bandage (sold under the name KPress®) that is elastic and self-adhesive and that is a long stretch bandage that serves to hold the first bandage in place and to apply pressure in addition to that of the first bandage in order to obtain the looked-for pressure.

The Coban 2 system is constituted by a first bandage that is put on without stretch, being made up of a foam that comes into contact with the skin in association with a self-adhesive bandage, and a second self-adhesive bandage that is a snort stretch bandage, that applies the looked-for pressure, and that serves to hold the system in place.

A drawback of those various systems is that in order to guarantee they are held in place and are effective, the self-adhesion of the bandages is obtained using adhesive or latex, which makes them more difficult to develop and can run the risk of allergy on contact with the skin, in particular when using natural rubber latex.

The role of the adhesive or the latex is nevertheless unavoidable, since it is what enables the bandage or the system to be kept in place after it has been wound around a limb, and to reduce the intrinsic relaxation that leads to loss of effectiveness and slipping over time along the limb.

In contrast, incorporating adhesive or latex makes manufacturing the products more complicated, since it modifies the pressure and the pressure difference properties of the bandage to which it is applied.

In order to improve acceptability for patients and care personnel, and in order to obtain a product that is easier to manufacture, it therefore appears desirable to have a compression system that makes use of bandages without adhesive or latex.

So-called "3D" knits are products that are in the form of two independent textile surfaces (knits) that are connected together by spacer yarns, whence the term "3D". By way of example, such products are used in the field of car seats because of their capacity for compression. However in order to obtain that capacity those knits are thick, rigid, and very elastic. Likewise, they are used in the field of textiles, e.g. for bra cups. Such knits are very soft to the touch, but once more very elastic in order to provide support. In neither situation are they appropriate for satisfying the properties of a compression bandage.

Other 3D knits that are suitable for compression are proposed in patent application WO 95/16416.

The problem which that application WO 95/16416 sets out to solve is eliminating cotton wool. Specifically, compaction of the cotton wool over time leads to slack between the leg and the bandage during movements, which can cause the arrangement to slip. The object is to compensate that compaction phenomenon by means of the 3D structure and of the thickness of the knit, making it possible to obtain a good padding effect and do without cotton wool. In order to achieve that result, the 3D knit described presents considerable weight and thicknesses. This leads to making compression bandages that are more voluminous and thus less easy to handle since they are in the form of thicker reels. They are also heavier, thereby increasing the risk of slipping more easily over time.

Thus, in order to mitigate that defect and the absence of latex or adhesive, Document WO 2009/71894 proposes incorporating an adhesive or latex to the 3D knit proposed in Document WO 95/16416, thereby likewise raising the above-mentioned difficulties relating to adhesive or latex in terms of developments and risk of allergy.

Patent application GB 2 473 321 proposes making 3D knits, still of considerable weight, in order to approach the padding role of cotton wool while applying pressures and pressure differences that are appropriate for the therapeutic targets. Nevertheless, all of the knits described are manufactured using "weft stitch" technology. From a point of view of industrial manufacture, that technology is not appropriate for making a compression bandage since cutting a 3D knit sheet leads to the product running. The problem of slipping over time is also present in products obtained in accordance with the teaching of that Document.

In order to remedy that, document GB 2 473 321 proposes making the 3D knit "cohesive" by adding silica derivatives alone or in association with latex or acrylates in order to provide retention over time, as mentioned at page 14 of that Document, thereby also giving rise to the above-mentioned problems in terms of development and risks of allergy.

The bandage is caused to slip by three fundamental factors.

The first factor is associated with the quality with which the bandage is put into place. If a bandage is put into place with too little stretch it runs the risk of slipping since the pressure applied on the limb is insufficient for holding it in place. A calibration device serves to solve this problem and to avoid the bandage conversely being stretched too much so that too great a pressure is applied, which could lead to forming a tourniquet. Likewise, it is necessary to secure the last turn in order to avoid the bandage from slackening at its end and then over the entire winding, which would lead to a loss of its therapeutic efficiency or even to it slipping along the leg. Various devices are used for ensuring it is well secured.

The second factor is associated with the ability of the bandage to withstand slipping on the skin, which depends on the state of its surface that comes into contact with the skin. This aspect is difficult to compensate since it is desired to have a skin-contacting face that presents a feel that is as little disagreeable as possible in order to encourage the patient to wear the bandage.

The third factor is associated with the way in which the bandage operates. It consists in finding a balance between the force applied by the stretched bandage during variation in the diameter of the calf and the capacity of the bandage for avoiding natural turn-on-turn slipping, as illustrated by the turns naturally becoming relaxed compared with when they were put into place. The same phenomenon is thus to be found as when the bandage has been put into place poorly, i.e. a loss of therapeutic effectiveness and possibly even vertical slipping of the bandage in the event of this lateral turn-on-turn slipping progressing over time, which can likewise lead to the bandage dropping. This phenomenon is amplified by the weight of the bandage.

This third factor, which leads to slipping, is particularly important and also represents the main reason why compression systems lose effectiveness over time.

Paradoxically, the cause of this slipping has not previously been studied in depth. In order to solve this problem and oppose this intrinsic relaxation, bandages have been made "cohesive", i.e. adhesive or latex has been preferentially applied on compression bandages. Thus, in all compression systems based on short stretch bandages, for which this phenomenon is the greatest, at least one cohesive bandage is included, once more leading to the above-defined problems.

In the absence of the bandage being made cohesive or of any other means for avoiding this phenomenon of slipping, and if the first two factors are under control, then the third factor becomes critical. The therapeutic effectiveness and the intrinsic relaxation of the bandage that increase the possibility of slipping are closely linked with this balance and the way it varies over time.

In conclusion, although the use of a 3D knit as a compression bandage has been proposed for almost 20 years, no solution appears to be completely satisfactory for obtaining a 3D knit that presents short stretch behavior in order to obtain the appropriate pressure difference, and that makes it possible, in the absence of latex or adhesive, to conserve that behavior and avoid any risk of the bandage slipping along the limb over time.

In order to solve these very complicated specifications with contradictory properties, the Applicant has studied the friction forces that apply to a bandage in contact with itself under the effect of pressure corresponding to the looked-for therapeutic treatment pressure, e.g. with a leg ulcer a pressure of about 35 mmHg to 50 mmHg. Specifically, the slipping of the turns of the bandage is associated with micro-movements of the bandage over itself, which micro-movements are imposed by its own weight due to gravity and by the repeated friction forces caused by variations in the diameter of the calf during movements.

In order to take measurements, which has never previously been envisaged, of these micro-movements of the bandage on itself, which movements are very small, the Applicant has used a rheometer, i.e. an apparatus that is used conventionally for measuring the rheological properties of soft materials. In addition to making it possible to determine very small forces, such apparatus also makes it possible to apply a shear torque, i.e. twisting, so as to be representative of the friction stresses that apply on the bandage both in its longitudinal direction and in its transverse direction. The technique as developed in this way has made it possible to determine the minimum shear force responsible for the first micro-movement to which the wound bandage is subjected that leads to lateral slipping of the turns and to the bandage relaxing. This shear force is referenced to as the "threshold" shear force since it measures the first micro-movement, and it is expressed in pascals (Pa).

These measurements have made it possible to obtain a better understanding of the phenomena involved and to determine the essential characteristics that need to be presented by a 3D knit in order to satisfy the above-enumerated properties, and in particular the threshold shear stresses that it needs to possess in order to avoid the intrinsic relaxing of the bandage so as to conserve its therapeutic effectiveness and avoid slipping.

The present invention thus relates to a bandage with longitudinal stretch lying in the range 30% to 160%, that is a 3D knit, being obtained using "warp stitch" technology, that is without any latex or adhesive, and that does not slip over at least for 48 hours, and better over at least for three or more days. Specifically, in the context of treating leg ulcers presenting wounds that are very exudative, these minimum durations of 48 and 72 hours correspond to the usual durations for changing the dressings that are placed under the compression bandages. It is therefore essential for the bandage to stay in place for at least 2 or 3 days without slipping.

SUMMARY OF THE INVENTION

The present invention thus relates to a compression bandage in the form of a knit obtained by warp stitch technology on the basis of synthetic yarns and comprising two textile surfaces of respective textile structures that may be identical or different, the surfaces being interconnected by spacer yarns, each textile surface including elastic yarns, said knit being characterized in that it presents longitudinal stretch measured in compliance with the standard EN 14704-1 lying in the range 30% to 160% and threshold shear stress greater than or equal to 2800 Pa, or greater than or equal to 3000 Pa.

Tests described below have shown that a bandage possessing such a threshold shear stress as a characteristic makes it possible to ensure there is no turn-on-turn slip of the compression bandage, thereby avoiding it relaxing intrinsically and thus enabling it to conserve its therapeutic effectiveness and prevent it from slipping.

In the present invention, the 3D knit may be for single use or it may be reusable, as thus consequently washable.

After the knitting operation, in order to stabilize the 3D knit, in particular in order to obtain a washable product, its structure should be "frozen" by using technologies commonly used for this purpose such as thermofastening by neat or aging. These operations consist in using an additional step, which may be in line with the knitting or separate therefrom, and in which the knit is caused to pass at a given speed and at a fixed temperature through an oven for thermofixing and through a stream of steam for aging.

In order to enhance accurate bandaging by care personnel, the compression bandage may be provided with calibration means. The calibration means may be visual, such as for example a set of regularly spaced apart pictograms printed on the bandage and made using a calibration system. Information about the recommended stretch during bandaging may be provided by the calibration means. Calibration may also be performed by care personnel using a stencil. This type of stencil or the explanations necessary for making it may be included in the packaging of the bandage. It is possible to use a kit having a plurality of bandages of different constitutions, of different widths, of different lengths, and/or provided with different calibrations for applying specific pressures.

The kit could also have one or more dressings for placing on the wound prior to putting on the bandage.

In order to facilitate handling while bandaging, a knit should be selected that presents longitudinal stretch as defined in the standard EN 14704-1 lying in the range 40% to 160%, or more precisely in the range 50% to 120%, or even more precisely in the range 55% to 100%.

By way of example, the knit may present thickness lying in the range 1 mm to 2 ram, or more precisely in the range 1 mm to 1.5 mm.

By way of example, the knit may present weight lying in the range 160 grams per square centimeter ($g/m^2$) to 370 $g/m^2$, or more precisely in the range 180 $g/m^2$ to 300 $g/m^2$, or even more precisely in the range 200 $g/m^2$ to 250 $g/m^2$.

Likewise and by way of example, the knit preferably presents spacing between its two textile faces lying in the range 0.4 mm to 1.5 mm, or more precisely in the range of 0.5 mm to 1.1 mm.

These low weight and low thickness properties make the compression bandage easier to use with shoes. The compression bandage can thus be used more easily with cotton wool, where necessary.

The two textile surfaces of the knit may have textile structures that are identical or different. These textile structures may be full or open.

Textile structures known as "open-work" and referred in the present application using the term "net" are well known to the person skilled in the art. An open-work knit is a knit presenting regular or irregular holes in its textile structure. These holes are obtained when one or more stitches in a column in the textile structure are not connected to stitches of the neighboring columns during knitting, typically by applying on a stitch diagram and/or acting on threading.

In an aspect of the present invention, the knit presents two textile surfaces of different textile structures, and in particular one textile surface that presents an open-work textile structure, referred to as the "net" face, and another textile surface that presents a full-face textile structure. The presence of a net face enhances the breathability of the bandage. Such a net face is typically placed in contact with a user's skin.

In a particular embodiment, said knit presents a face with a textile structure of one of the following types: charmeuse; open or closed loop single knit; atlas in one or more rows; closed or open loop or alternating closed loop and open loop pillar stitch. Said face is opposite to the face that is to be put into contact with the skin, which face has a textile structure that is a net, with a textile structure of the same type or of a different type, but that is an open-work structure.

In order to make it easier to go past the heel and avoid necking of the bandage while it is being put into place, it is possible to use 3D knits that present transverse stretch not less than 120% as measured in compliance with method A § 9.1 of the standard EN 14704-1, e.g. lying in the range 120% to 300%, or indeed in the range 120% to 250%.

By way of example, knits of the invention are made using yarns commonly used for making textile products, and in particular knits. By way of example, the yarns may be synthetic. These yarns come in two major categories: elastic yarns and thermoplastic yarns.

By way of example of elastic yarns, mention may be made of yarns based on polyurethane fibers such as spandex yarns sold under the name Lycra, yarns based on elastodiene, or yarns based on triple block polymers (styrene-ethylene-butylene-styrene). Among thermoplastic yarns, mention may be made of yarns based on synthetic materials that are not elastomers, such as for example polyester, polyamide, polypropylene, polybutylene terephthalate (PBT).

All of these thermoplastic yarns may optionally be plated, and they may optionally be textured.

By way of example, the two textile surfaces of the 3D knit are made using elastic yarns and thermoplastic yarns. These yarns may be single filament or multifilament. These textile surfaces may be made from yarns that are identical or different. The two surfaces preferably include elastic yarns that are similar.

By way of example, the elastic yearns present in these textile surfaces may present weights of about 40 decitex (dtex) to 80 dtex, and the thermoplastic yarns may present weights of about 40 dtex to 90 dtex.

If it is desired to enhance the transfer of moisture through the knit to the outside, it is possible to use yarns of a non-synthetic nature, e.g. such as cotton or viscose, in one or both faces, and in particular in the face in contact with the skin.

By way of example, the elastic yarns may comprise spandex yarns and the thermoplastic yarns may comprise polyamide or polyester yarns.

The spacer yarns are typically single filament thermoplastic yarns, such as polyester or polyamine yarns, e.g. presenting weight lying in the range dtex to 80 dtex, or indeed 40 dtex to 70 dtex, or more particularly a polyester single filament presenting weight in the range 44 dtex to 55 dtex.

For knitting the 3D knit, it is possible by way of example to use a single bar for knitting the spacer yarn that links together the two textile surfaces.

The invention also provides a kit comprising one or more compression bandages as defined above, together with one or more dressings suitable for placing on a wound prior to putting one of the compression bandage into place.

DETAILED DESCRIPTION

Figure 2:
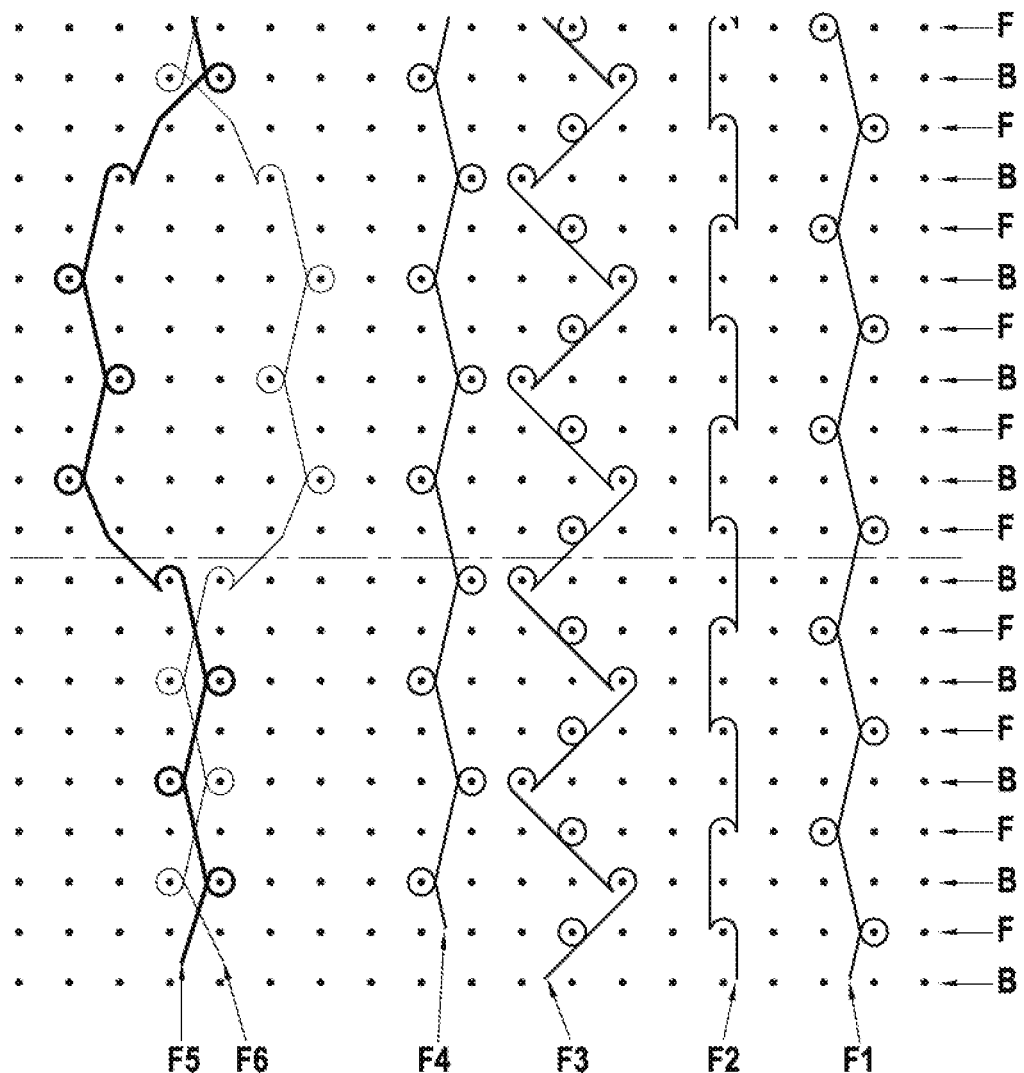
Figure 3:
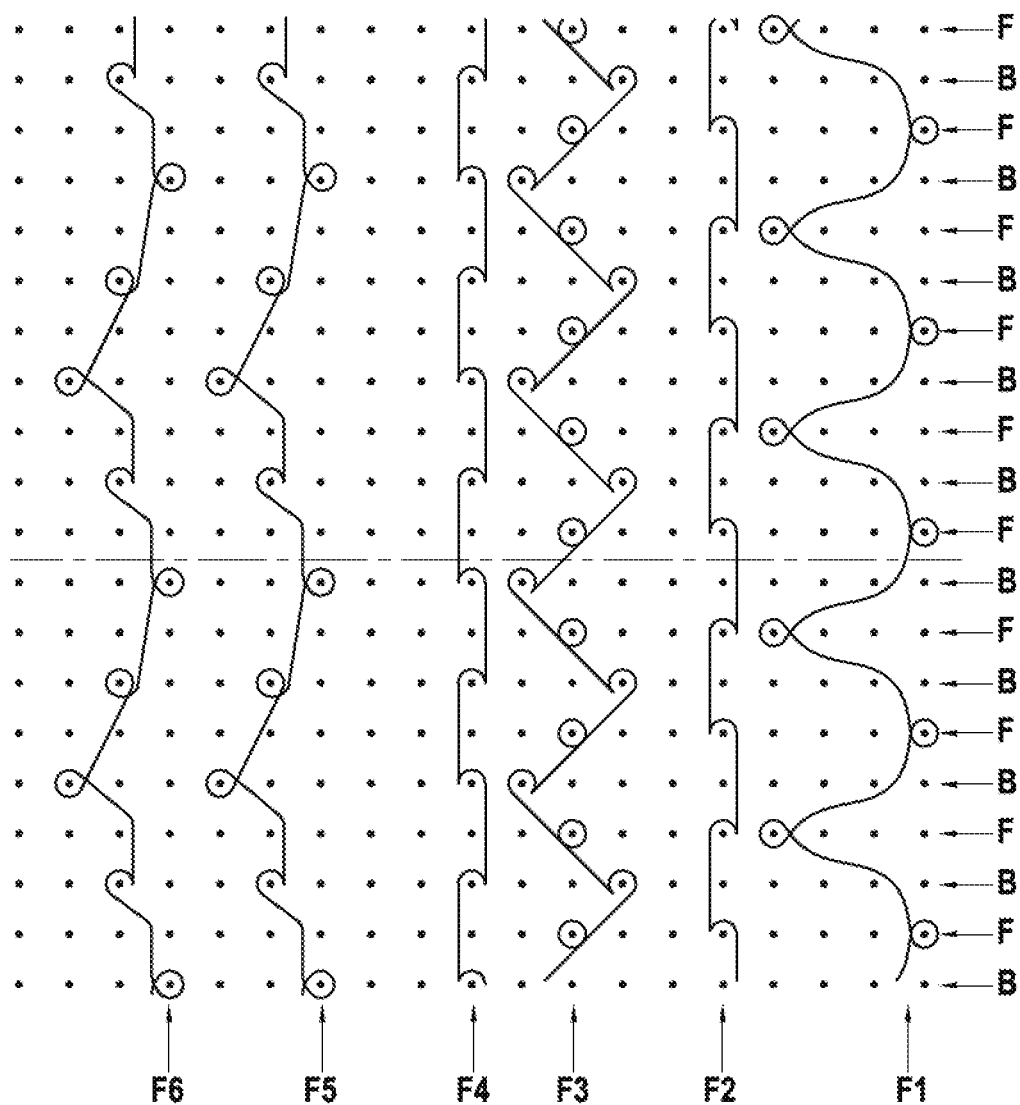

The invention is illustrated by the following examples and comparative tests, and also by FIGS. 1, 2, and 3.

EXAMPLE EMBODIMENT OF THE INVENTION

A knit of the invention having a width of about centimeters (cm) has been made on a 22 gauge double-needle bed Raschel warp knitting machine.

In order to perform the knitting, six bars were used in compliance with the stitch diagram shown in FIG. 1 using the following yarns and conditions:

Nature of the Yarns
  F1: polyamide yarn sold by the supplier Radici under the reference 78/18/1 dtex S Beige;
  F2: 44 dtex spandex yarns sold by the supplier Asahi Kasei Group;
  F3: yarn in the form of a 55 dtex polyester monofilament sold by the supplier Filva;
  F4: 44 dtex spandex yarn sold by the supplier Asahi Kasei Group;
  F5: polyamide 66 yarn sold by the supplier Emile Tardy under the reference PA 66 1/44/34/FT BE MM; and
  F6: polyamide 66 yarn sold by the supplier Emile Tardy under the reference PA 66 1/44/34/FT BE MM.

Settings of the Knitting Machine
  F1: feed 2500 mm of yarns consumed for making 480 stitches-full threading;
  F2: feed 1500 mm of yarns consumed for making 480 stitches-threading 1 full/1 empty;
  F3: feed 3500 mm of yarns consumed for making 480 stitches-full threading;
  F4: feed 1600 mm of yarns consumed for making 480 stitches-threading 1 full/1 empty;
  F5: feed 2250 mm of yarns consumed for making 480 stitches-threading 3 full/1 empty; and
  F6: feed 2250 mm of yarns consumed for making 480 stitches-threading 3 full/1 empty.

Stitch Diagram

FIG. 1 is a diagram showing an example stitch structure for making a knit in a particular embodiment of the invention.

In this figure, the front needle bed has reference F and the back needle bed has reference B. The stitch diagrams for the yarns F1 to F6 are shown.

It should clearly be understood that this example, and those that follow, are purely illustrative, and that they should not be interpreted in a manner that is limiting on the scope of the invention.

The knit as made in this way was subjected to a step of in-line heat treatment.

During this step, the knit passed once through two rollers formed by heater cylinders so that each of its faces was subjected to the treatment at a speed of 5.5 meters per minute (m/min). Before passing the knit, the temperature of the cylinders was set to about 190° C.

The following techniques were used for evaluating the parameters of the resulting knit.

Measuring Weight

Weight was measured in compliance with the standard NF EN 12127. Five testpieces each having an area of 100 square centimeters (cm$^2$) (measured to within ±1%) were weighed using scales of precision at best 1 milligram (mg).

Weighing was performed at a temperature of 21° C.±2° C. and relative humidity (RH) of 60%±15%.

The final measurement was the average of the five testpieces.

Measuring Thickness

Thickness was measured in compliance with the standard NF EN ISO 9073-2. A Keyence laser micrometer was used (having a CCD LK-G87 laser sensor head and a CCD LK-G3001PV laser movement sensor). The application pressure was set at 0.5 kilopascals (kPa) and the area of the steel disk was 2500 square millimeters (mm$^2$).

Measuring Spacing between the Faces

This measurement was performed as follows.

Using a Keyence digital microscope (with ×100 or ×200 lenses) the space was determined between the two planes of the two textile surfaces.

The mean plane of each of the two surfaces was marked by a horizontal line estimated by the operator and the distance between the two lines was determined automatically by the software. The measurement was repeated several times in order to increase accuracy and the resulting measurements were averaged.

Measuring Threshold Shear Stress

The measurements were performed using a DHR2 rheometer sold by the supplier TA Instruments.

They were performed at a temperature of 35° C. (so as to be close to the temperature of the bandages in contact with the skin), said temperature being regulated on a Peltier plate forming part of the rheometer.

Two disks having a diameter of 25 mm were cut out from the 3D knit under analysis.

A fine and rigid double-sided adhesive sold by the supplier Plasto under the reference P753 was used to stick the two disks respectively to the metal face of the movable plate and to the Peltier plate of the rheometer. The two 3D knit disks were put into contact, the charmeuse structure face (also known as a locknit structure face) contacting the net structure face, while applying a pressure of 5.3 kPa (i.e. the equivalent of 40 mmHg). The program controlling the rheometer generates a stress slope (torque) varying from 100 Pa to 10,000 Pa in 600 seconds (s). The apparatus records the first micro-movement that it detects, which corresponds to the threshold shear stress expressed in Pa.

It is considered that the instrumental uncertainty on this measurement is plus or minus 6%.

The parameters of the resulting knit were as follows (Example 1):
- weight: 232 g/m$^2$;
- thickness: 1.23 mm;
- threshold shear stress: 3080 Pa;
- spacing between faces: 0.64 mm;
- longitudinal stretch in compliance with the standard EN 14704-1: 56%;
- transverse stretch in compliance with the standard EN 14704-1: 128%.

Several other knit examples were also made, as set out in detail below.

These other examples were made using a stitch diagram identical to that shown in FIG. 1 (except where specified to the contrary). There follows a detailed description of the natures of the yarns and of the settings of the knitting machine, and also of the characteristics that were obtained.

Example 2: e.g. Corresponding to a Product Having a Full Face in Contact with a Subject's Skin, and an Opposite Face that was a Net Nature of the Yarns
- F1: polyamide yarn sold by the supplier Radici under the reference 78/24/1 dtex S Beige;
- F2: 44 dtex spandex yarns sold by the supplier Asahi Kasei Group;
- F3: yarn in the form of a 55 dtex polyester monofilament, sold by the supplier Filva;
- F4: 44 dtex spandex yarn sold by the supplier Asani Kasei Group;
- F5: polyamide 66 yarn sold by the supplier Emile Tardy under the reference PA 66 1/44/34/FT BE MM; and
- F6: polyamide 66 yarn sold by the supplier Emile Tardy under the reference PA 66 1/44/34/FT BE MM.

Settings of the Knitting Machine
- F1: feed 2000 mm of yarns consumed for making 480 stitches-full threading;
- F2: feed 1500 mm of yarns consumed for making 480 stitches-threading 1 full/1 empty;
- F3: feed 3500 mm of yarns consumed for making 480 stitches-full threading;
- F4: feed 1600 mm of yarns consumed for making 480 stitches-threading 1 full/1 empty;
- F5: feed 2150 mm of yarns consumed for making 480 stitches-threading 3 full/1 empty; and
- F6: feed 2250 mm of yarns consumed for making 480 stitches-threading 3 full/1 empty.

The knit as made in this way was subjected to an in-line heat treatment step.

During this step, the knit passed once between two rollers formed by heater cylinders so that each face was subjected to the treatment at a speed of 5.5 m/min. The temperature of the cylinders before passing the knit was set to about 190° C.

Characteristics of the Resulting Product: (Example 2)
- Weight: 2.31 g/m$^2$.
- Thickness: 1.22 mm.
- Threshold shear stress: 3027 Pa.
- Spacing between faces: 0.52 mm.
- Longitudinal stretch in compliance with the standard EN 14704-1: 62%.
- Transverse stretch in compliance with the standard EN 14704-1: 173%.

Example 3: e.g. Corresponding to a Long Stretch Product

Nature of the Yarns
- F1: polyamide 66 yarn sold by the supplier Emile Tardy under the reference PA 66 1/44/34/FT BE MM.
- F2: 44 dtex spandex yarns sold by the supplier Asahi Kasei Group.
- F3: yarn in the form of a 55 dtex polyester monofilament, sold by the supplier Filva.
- F4: 44 dtex spandex yarn sold by the supplier Asani Kasei Group.
- F5: polyamide 66 yarn sold by the supplier Emile Tardy under the reference PA 66 1/44/34/FT BE MM.
- F6: polyamide 66 yarn sold by the supplier Emile Tardy under the reference PA 66 1/44/34/FT BE MM.

The mesh diagram in this example was different from the other examples, and is shown in FIG. 2.

Settings of the Knitting Machine
- F1: feed 2100 mm of yarns consumed for making 480 stitches-full threading.
- F2: feed 2050 mm of yarns consumed for making 480 stitches-full threading.
- F3: feed 3700 mm of yarns consumed for making 480 stitches-full threading.
- F4: feed 2300 mm of yarns consumed for making 480 stitches—full threading.
- F5: feed 2150 mm of yarns consumed for making 480 stitches-threading 3 full/1 empty.
- F6: feed 2150 mm of yarns consumed for making 480 stitches-threading 3 full/1 empty.

The knit as made in this way was subjected to an in-line heat treatment step.

During that step the knit was passed once between two rollers formed by heater cylinders so that each face was subjected to the treatment, at a speed of 5.9 meters per hour (m/h). The temperature of the cylinders prior to passing the knit was set to about 70° C., A strip of product as obtained in that way was then subjected to five successive washes without drying between the washes in a washing machine at 40° C. and at 800 revolutions per minute (rpm), with a washing product sold under the trademark "Le Chat machine".

Characteristics of the Resulting Product: (Example 3)
- Weight: 367 g/m$^2$.
- Thickness: 1.9 mm.

Threshold shear stress: 4077 Pa.
Spacing between faces: 1.08 mm.
Longitudinal stretch in compliance with the standard EN 14704-1: 111%.
Transverse stretch in compliance with the standard EN 14704-1: 191%.

Example 4: Corresponding for Example to a Product Having a 22 Dtex Spacer Yarn

Nature of the Yarns
  F1: polyamide yarn sold by the supplier Radici under the reference 78/18/1 dtex S Beige;
  F2: 44 dtex spandex yarns sold by the supplier Asahi Kasei Group;
  F3: yarn in the form of a 22 dtex polyester monofilament sold by the supplier Filva;
  F4: 44 dtex spandex yarn sold by the supplier Asahi Kasei Group;
  F5: polyamide 66 yarn sold by the supplier Emile Tardy under the reference PA 66 1/44/34/FT BE MM; and
  F6: polyamide 66 yarn sold by the supplier Emile Tardy under the reference PA 66 1/44/34/FT BE MM.
Settings of the Knitting Machine
  F1: feed 2400 mm of yarns consumed for making 480 stitches-full threading;
  F2: feed 1600 mm of yarns consumed for making 480 stitches-threading 1 full/1 empty;
  F3: feed 3900 mm of yarns consumed for making 480 stitches-full threading;
  F4: feed 1600 mm of yarns consumed for making 480 stitches-threading 1 full/1 empty;
  F5: feed 2000 mm of yarns consumed for making 480 stitches-threading 3 full/1 empty; and
  F6: feed 2000 mm of yarns consumed for making 480 stitches-threading 3 full/1 empty.

The knit as made in this way was subjected to an in-line heat treatment step.

During that step the knit was passed once between two rollers formed by heater cylinders so that each face was subjected to the treatment at a speed of 5.5 m/min. The temperature of the cylinders before passing a knit was set to about 190° C.

Characteristics of the Resulting Product: (Example 4)
  Weight: 199 g/m$^2$.
  Thickness: 1.1 mm.
  Threshold shear stress: 3007 Pa.
  Spacing between faces: 0.57 mm.
  Longitudinal stretch in compliance with the standard EN 14704-1: 54%.
  Transverse stretch in compliance with the standard EN 14704-1:192%.

Example 5: Corresponding for Example to a Product without an Open-Work Face, i.e. with Two Full Faces Nature of the Yarns
  F1: polyamide yarn sold by the supplier Radici under the reference 78/18/1 dtex S Beige;
  F2: 44 dtex spandex yarns sold by the supplier Asahi Kasei Group;
  F3: yarn in the form of a 55 dtex polyester monofilament sold by the supplier Filva;
  F4: 44 dtex spandex yarn sold by the supplier Asahi Kasei Group;
  F5: polyamide 66 yarn sold by the supplier Emile Tardy under the reference PA 66 1/44/34/FT BE MM;
  F6: polyamide 66 yarn sold by the supplier Emile Tardy under the reference PA 66 1/44/34/FT BE MM.

The stitch diagram in this example is different from that of the other examples, and is shown in FIG. 3.

Settings of the Knitting Machine
  F1: feed 3200 mm of yarns consumed for making 480 stitches-full threading.
  F2: feed 1600 mm of yarns consumed for making 480 stitches-threading 1 full/1 empty.
  F3: feed 3500 mm of yarns consumed for making 480 stitches-full threading.
  F4: feed 1700 mm of yarns consumed for making 480 stitches-threading 1 full/1 empty.
  F5: feed 1900 mm of yarns consumed for making 480 stitches-threading 3 full/1 empty.
  F6: feed 1900 mm of yarns consumed for making 480 stitches-threading 3 full/1 empty.

The knit as made in this way was subsequently subjected to an in-line heat treatment step.

During that step the knit was passed once between two rollers formed by heater cylinders so that each face was subjected to the treatment at a speed of 5 m/min. The temperature of the cylinders before passing the knit was set to about 190° C.

Characteristics of the Resulting Product: (Example 5)
  Weight: 262 g/m$^2$.
  Thickness: 1.2 mm.
  Threshold shear stress: 3027 Pa.
  Spacing between faces: 0.76 mm,
  Longitudinal stretch in compliance with the standard EN 14704-1:43%.
  Transverse stretch in compliance with the standard EN 14704-1:127%.

Thereafter, in vitro pressure performance was compared using the test described below between the examples of the invention and the two-layer compression system sold under the name K2 by the supplier Laboratoires URGO.

In Vitro Test

The performance of each of the 3D knit of Examples 1 to 5 and of the two-layer compression system sold under the name K2 by the supplier Laboratoires URGO was evaluated in terms of working and rest pressures and of pressure difference, over time.

Use was made of the in vitro test method and apparatus described in patent application WO 2007/113430 page 17, line 26 to page 19, line 18. In that method, the bandage is placed around a cylinder with total coverage of 100%, and then the circumference of the cylinder is caused to vary at a speed that is imposed continuously between a "rest" pressure (smallest diameter) and a "working" pressure (greatest diameter) in order to mimic muscular contraction. Pressure sensors measured the rest pressure and working pressure values over time.

The time interval between measuring working pressure and rest pressure was 5 s, and the frequency with which these two parameters were measured in succession was 0.2 hertz (Hz).

In order to test the compression bandages of the invention, the stretch of the bandage on being put into place was determined as a function of the looked-for working pressure, e.g. using the rupture traction curve as defined in the standard EN ISO 13934-1. In application of Laplace's law, the stretch to be applied corresponds to the looked-for pressure.

A rectangular bandage of sufficient width was prepared, by fraying if necessary, in order to obtain a sample having a final width of 50 mm. The sample was placed in the jaws of a CRE testing machine that were spaced apart by 200 mm. The traction test was performed until the sample ruptured at the speed of 100 mm/min. The test was repeated for five samples. Conditions relating to conditioning, relative humidity, and temperature were as defined in the standard EN ISO 13934-1.

It was thus determined that stretch during bandaging should be 40% for the bandage of Examples 1 to 3, 45% for the bandage of Example 4, and 30% for the bandage of Example 5 of the invention in order to apply a maximum pressure of about 50 mmHg to 70 mmHg on bandaging.

In order to bandage properly, the bandages were calibrated using a stencil as described in patent-application WO 2007/113340 on page 13, line 18 to page 14, line 6.

The results obtained for the bandage obtained as examples of the invention and for the two-layer compression system sold by the supplier Laboratoires URGO under the name K2, of size 18 cm-25 cm are summarized in Tables 1 and 2 below.

The value "max pressure at T0" corresponds to the first working pressure measured immediately after bandaging, and "delta at T0" corresponds to the pressure difference between the first working pressure and the first rest pressure measured immediately after bandaging. The values "max pressure at T24" and "delta at T24" correspond to the measurements taken 24 hours after bandaging, as measured in mmHg. Thereafter, the difference between T0 and T24 was calculated as "delta (T0-T24)".

TABLE 1

| Example 1 | Example 2 | K2 (Laboratoires URGO) | Measurement taken |
|---|---|---|---|
| 40% | 40% | 55% + 50% | Stretch on bandaging |
| 69 | 63 | 44 | Max pressure at T0 |
| 28 | 25 | 19 | Delta at T0 |
| 51 | 45 | 35 | Max pressure at T24 |
| 95 | 21 | 17 | Delta at T24 |
| +3 | +4 | +2 | Delta (T0-T24) |

TABLE 2

| Example 3 | Example 4 | Example 5 | Measurement taken |
|---|---|---|---|
| 40% | 45% | 30% | Stretch on bandaging |
| 52 | 71 | 50 | Max pressure at T0 |
| 15 | 31 | 26 | Delta at T0 |
| 44 | 52 | 34 | Max pressure at T24 |
| 21 | 26 | 20 | Delta at T24 |
| −6 | +5 | +6 | Delta (T0-T24) |

These tables snow that results obtained in terms of pressure applied at 24 h and pressure difference at 24 h both for the K2 two-layer system and for the single bandages of the invention that lie within the intended ranges, i.e. a maximum pressure at 24 h lying in the range 34 mmHg to 50 mmHg and a pressure difference at 24 h lying in the range 15 mmHg to 25 mmHg.

The pressure difference values at 24 h, which are important for the effectiveness of the treatment, are even better with the single bandages of the invention, i.e. 20 mmHg to 26 mmHg as compared with 17 mmHg for the K2 two-layer system. It can also be seen that for all of the products in Examples 1, 2, 4, and 5, and for the product K2, which are all short stretch products, this pressure difference varied little over time since the variation was in the range +3 to +6 for the knits of the invention and +/2 for the K2 two-layer system.

Surprisingly, Example 3, which is a long stretch product, and thus expected to be less effective in terms of pressure difference, also presented an excellent pressure difference of 21 mmHz. Furthermore, the pressure difference improved over time and it was clearly better at 24 h than at T=0; 21 mmHg as compared with 15 mmHg.

In conclusion, the bandages of the invention make it possible to obtain therapeutic properties that are equivalent to those of the K2 product, or even better, while conserving these properties over time, and doing so with only one bandage and without adding latex or adhesive.

In the same manner, Example 1 and the K2 product were compared using the in vivo test described below in order to evaluate the intrinsic relaxation of the bandages over time.

This in vivo test was performed as follows.

The bandages were wound around the leg in compliance with the recommendations set out in the instructions for the K2 two-layer system.

For reference, those instructions recommend the following method of application:

1) Hold the foot at 90°, toes pointing upwards. Apply Ktech to the base of the toes by making two anchor holes, and ensure that the cotton wool face is in direct contact with the skin and the pressure indicator is situated on the top side of the bandage. Continue making a "figure of 8" around the ankle without applying excessive tension on the foot and cover the heel thoroughly.

2) Go up to the knee making spiral turns and stretching the bandage appropriately: the pressure indicator printed on the bandages should be circular in shape. In order to obtain proper overlap, the pressure indicator should be just covered (50% overlap). Finish 2 cm below the knee and cut off excess bandage. Secure using sticking plaster.

3) Apply Kpress on Ktech using the same technique, beginning one finger above Ktech and ending one finger below Ktech so that only Ktech is in direct contact with the skin. Once applied, press gently on the bandage with the hands in order to ensure that the system stays properly in place.

It can readily be understood that the last step 3) is not needed for a compression bandage of the invention.

In the example of the invention, the stretch on putting into place was 40% as above in the in vitro test, and the knit was calibrated in the same manner. The bandages were wound around the foot, the heel, and along the leg up to the knee with one layer overlapping another by 50%. The last turn was secured to itself using a metal fastener or sticking plaster. If it is desired to verify the pressure being applied by the bandage, it is possible to place an interface pressure measuring sensor (such as for example the sensor referenced KKH-01 from the supplier Kikuhime) at a point B1 that corresponds to the zone where the Achilles tendon transforms into calf muscle, i.e. generally speaking about 10 cm to about 15 cm above the malleolis. A vertical line is drawn using a fine permanent felt tip over at least three turns along the axis of the tibial crest, starting from the last-wound turn. At the end of the duration of the test, this mark serves as a reference for evaluating the horizontal shift of the line by using a ruler graduated in mm. During movements, the line ceases to be rectilinear and presents steps that are offset to a greater extent when the turn-on-turn slip is considerable. If the turn-on-turn slipping is very small or non-existent, then the vertical line remains intact or varies very little, mainly over the first turn which is situated under the last wound turn.

This offset of the vertical line is representative of the relaxation of the bandage and illustrates its potential slip over time.

The test was performed for 6 hours on five people. On one leg, each person wore a 10 cm wide and 2.6 cm long bandage in accordance with Example 1, the net face in contact with the skin, calibrated at 40% on being put into place, and on the other leg, each person wore the K2 two-layer system.

After 6 hours, the offset of the vertical line on the first three turns was measured.

The results were as follows:

K2 two-layer system: no offset of the line on any turn. This result is to be expected as a result of the bandage being made "cohesive", thereby preventing the turns from slipping one on another.

Compression bandage in accordance with Example 1: no offset of the line on turns 2 and 3 and a small mean offset of 4 mm on the first turn situated under the last turn to be wound.

This mean value is negligible and represents measurement fluctuations associated with variations in the calves of the testers, with the reproducibility with which the bandaging was performed, and with manufacturing variabilities for the bandages.

It can thus be considered that the bandage of the invention presents resistance to turn-on-turn slip that is equivalent to that of the cohesive system.

This test shows that in terms of ability to remain in place, the two products are equivalent.

Using the same protocol, the bandage of Example 5 calibrated at 30% on being bandaged as described above for the in vitro test was tested on a single person. The only difference was that the last turn was secured to itself using two Velcro strips instead of a metal fastener.

After a duration of 6 hours, it was observed once more that there was a small offset of the line through 3 mm on the first turn situated under the last-wound turn. An offset of 1 mm was measured on turn 2 (which represents uncertainty on evaluating the measurement of the thickness of the line, and is therefore negligible), and no offset was observed on turn 3.

It can thus be considered that the bandage of Example 5 presents the ability to withstand turn-on-turn slip that is equivalent to that of Example 1.

Together these tests show that by using a single bandage, a compression device is indeed obtained that presents good therapeutic properties and that does not slip over time, and that this is achieved without adding additional substances to the bandage.

The invention claimed is:

1. A compression bandage in the form of a single knit obtained by warp stitch technology, the single knit consisting of synthetic yarns and comprising two textile surfaces of respective textile structures that may be identical or different, the two textile surfaces being interconnected by spacer yarn of the synthetic yarns, each of the two textile surfaces including elastic yarn of the synthetic yarns, said single knit not including adhesive and not including latex, and said single knit having:
 a longitudinal stretch measured in compliance with the standard EN 14704-1 lying in the range 30% to 160%, and
 a threshold shear stress of greater than or equal to 2800 Pa, wherein the threshold shear stress is a minimum shear stress that causes lateral slipping between two exterior faces of the single knit when pressed against each other with a force of 5.3 kPa, the two exterior faces respectively provided by the two textile surfaces, wherein
 the spacer yarn is a monofilament that presents weight lying in the range 20 dtex to 80 dtex,
 the single knit presents weight lying in the range 160 g/m² to 370 g/m² and a thickness lying in the range 1 mm to 2 mm,
 the elastic yarn in one of the two textile surfaces presents weight lying in the range 40 dtex to 80 dtex, and
 the two textile surfaces include thermoplastic yarns of the synthetic yarns presenting weights lying in the range 40 dtex to 90 dtex.

2. A compression bandage according to claim 1, wherein the single knit presents spacing between the two textile surfaces lying in the range 0.4 mm to 1.5 mm.

3. A compression bandage according to claim 2, wherein the single knit presents the spacing between the two textile surfaces lying in the range 0.5 mm to 1.1 mm.

4. A compression bandage according to claim 1, wherein the spacer yarn presents weight lying in the range 40 dtex to 70 dtex.

5. A compression bandage according to claim 1, wherein
 a first exterior face of the two exterior faces has a textile structure that is at least one selected from the following list:
 charmeuse,
 open or closed loop,
 atlas in one or more rows, and
 closed or open loop or alternating closed loop and open loop pillar stitch,
 the first exterior face being opposite to a second exterior face of the two exterior faces that is to be put into contact with the skin, the second exterior face having a textile structure that is a net, presenting an open-work textile structure.

6. A compression bandage according to claim 1, wherein the single knit presents thickness lying in the range 1 mm to 1.5 mm.

7. A compression bandage according to claim 1, wherein the single knit presents weight lying in the range 160 g/m² to 300 g/m².

8. A compression bandage according to claim 1, wherein the single knit presents longitudinal stretch as defined in the standard EN 14704-1 lying in the range 50% to 120%.

9. A compression bandage according to claim 1, wherein the single knit is fabricated using a single bar for the spacer yarn that connects together the two textile surfaces.

10. A kit comprising one or more compression bandages according to claim 1 and one or more dressings adapted to be placed on a wound prior to putting the compression bandage into place.

11. A compression bandage according to claim 1, wherein the single knit when wound around itself results in the two exterior faces being disposed in consecutive wraps of the single knit and in contact with each other.

* * * * *